United States Patent
Zeller

(10) Patent No.: US 10,386,443 B2
(45) Date of Patent: Aug. 20, 2019

(54) METHOD FOR CALIBRATION IN A MAGNETIC RESONANCE IMAGING PROCEDURE

(71) Applicant: Siemens Healthcare GmbH, Erlangen (DE)

(72) Inventor: Mario Zeller, Erlangen (DE)

(73) Assignee: Siemens Healthcare GmbH, Erlangen (DE)

( * ) Notice: Subject to any disclaimer, the term of this patent is extended or adjusted under 35 U.S.C. 154(b) by 0 days.

(21) Appl. No.: 16/000,723

(22) Filed: Jun. 5, 2018

(65) Prior Publication Data

US 2018/0356488 A1    Dec. 13, 2018

(30) Foreign Application Priority Data

Jun. 13, 2017  (DE) .......................... 10 2017 209 988

(51) Int. Cl.
*G01R 33/58* (2006.01)
*A61B 5/055* (2006.01)
(Continued)

(52) U.S. Cl.
CPC ............ *G01R 33/583* (2013.01); *A61B 5/055* (2013.01); *G01R 33/4818* (2013.01);
(Continued)

(58) Field of Classification Search
CPC .............. G01R 33/583; G01R 33/5611; G01R 33/4835; G01R 33/4818; G01R 33/5615; A61B 5/055
See application file for complete search history.

(56) References Cited

U.S. PATENT DOCUMENTS 5,825,185 A * 10/1998 Liu ................... G01R 33/56554
                                                    324/309
6,249,595 B1 * 6/2001 Foxall .............. G01R 33/56554
                                                    382/128
(Continued)

FOREIGN PATENT DOCUMENTS

DE     102015207591 A1    10/2016
DE     102015218106 B4     5/2017

OTHER PUBLICATIONS

Setsompop, Kawin et al. "Blipped-Controlled Aliasing in Parallel Imaging (blipped-CAIPI) for simultaneous multi-slice EPI with reduced g-factor penalty"; in: Magnetic Resonance in Medicine; vol. 67; No. 5; pp. 1210-1224; (2012).

(Continued)

*Primary Examiner* — Dixomara Vargas
(74) *Attorney, Agent, or Firm* — Lempie Summerfield Katz LLC

(57) ABSTRACT

The disclosure relates to a method for calibration in a magnetic resonance (MR) imaging procedure, in which MR imaging data is acquired simultaneously from a multiplicity of slices of a subject under examination, wherein at least one subsampled calibration dataset is generated from a fully sampled reference dataset of an individual slice by rearranging an order of the data points in the reference dataset. In addition, a reconstruction dataset, which is used to assign MR imaging data to the individual slice, is calculated based on the rearranged order of the at least one calibration dataset, wherein the MR imaging data of the individual slice is subsampled in k-space.

20 Claims, 3 Drawing Sheets

(51) Int. Cl.
*G01R 33/483* (2006.01)
*G01R 33/561* (2006.01)
*G01R 33/48* (2006.01)

(52) U.S. Cl.
CPC ...... *G01R 33/4835* (2013.01); *G01R 33/5611* (2013.01); *G01R 33/5615* (2013.01)

(56) References Cited

U.S. PATENT DOCUMENTS

| | | | | |
|---|---|---|---|---|
| 6,593,741 B2* | 7/2003 | Bydder | ................ | G01R 33/54 324/307 |
| 6,794,867 B1* | 9/2004 | Block | ................ | G01R 33/4828 324/307 |
| 7,148,685 B2* | 12/2006 | Block | ................ | G01R 33/4828 324/307 |
| 7,863,893 B2* | 1/2011 | Griswold | ........... | G01R 33/5611 324/307 |
| 8,692,549 B2* | 4/2014 | Grady | ................ | G01R 33/5611 324/307 |
| 8,854,040 B2* | 10/2014 | Kannengiesser | .. | G01R 33/5611 324/309 |
| 9,069,051 B2* | 6/2015 | Griswold | ........... | G01R 33/4826 |
| 9,575,153 B2* | 2/2017 | Simonetti | ........... | G01R 33/4828 |
| 9,588,208 B2* | 3/2017 | Polimeni | .......... | G01R 33/56509 |
| 9,739,857 B2* | 8/2017 | Porter | ................ | G01R 33/4818 |
| 2008/0278160 A1* | 11/2008 | Griswold | ........... | G01R 33/5611 324/307 |
| 2012/0019246 A1* | 1/2012 | Kannengiesser | .. | G01R 33/5611 324/309 |
| 2013/0249553 A1* | 9/2013 | Simonetti | .......... | G01R 33/4828 324/309 |
| 2014/0015527 A1* | 1/2014 | Griswold | ........... | G01R 33/4826 324/309 |
| 2014/0197834 A1* | 7/2014 | Porter | ................ | G01R 33/4818 324/309 |
| 2014/0292330 A1* | 10/2014 | Gulani | ............... | G01R 33/3614 324/309 |
| 2014/0294734 A1* | 10/2014 | Gulani | ............... | G01R 33/3614 424/9.32 |
| 2014/0296700 A1* | 10/2014 | Gulani | ............... | G01R 33/3614 600/414 |
| 2015/0115958 A1 | 4/2015 | Wang et al. | | |
| 2015/0285891 A1* | 10/2015 | Dannels | ........... | G01R 33/56554 324/309 |
| 2015/0323634 A1* | 11/2015 | Polimeni | .......... | G01R 33/56509 324/309 |
| 2015/0362576 A1* | 12/2015 | Jurrissen | ........... | G01R 33/445 324/309 |
| 2016/0313433 A1 | 10/2016 | Beck | | |
| 2017/0074960 A1* | 3/2017 | Bhat | ................. | G01R 33/5616 |
| 2017/0082718 A1 | 3/2017 | Beck | | |

OTHER PUBLICATIONS

German Office Action for related German Application No. DE 102017209988.7, dated Jan. 11, 2018, with English translation.
Decision to Grant Patent for related German Application No. DE 102017209988.7 dated Feb. 23, 2018, with English translation.

* cited by examiner

ID FOR CALIBRATION IN A
MAGNETIC RESONANCE IMAGING
PROCEDURE

The application claims the benefit of German Patent Application No. DE 10 2017 209 988.7, filed Jun. 13, 2017, which is hereby incorporated by reference in its entirety.

TECHNICAL FIELD

The present disclosure relates to a method for calibration in a magnetic resonance (MR) imaging procedure, in which MR imaging data is acquired simultaneously from a multiplicity of slices of a subject under examination. The disclosure also relates to the associated magnetic resonance system for performing the method. A computer program product and an electrically readable data storage medium are also provided.

BACKGROUND

Various techniques are known for reducing the measurement time needed for MR imaging. For instance, techniques are known for exciting the core magnetization simultaneously in a plurality of slices of the region under examination and acquiring MR imaging data simultaneously from the plurality of slices. Such techniques may be referred to as simultaneous multislice (SMS) imaging.

There are a large number of different methods for performing SMS imaging. A parallel imaging technique called partial parallel acquisition (PPA) is conventionally used to separate the MR imaging data and includes a slice-specific reconstruction dataset for each of the slices. A recently introduced method is the method introduced by Setsompop et al. (MRM 2012), "Blip-controlled aliasing in parallel imaging" (Blipped-CAIPI), which is described in more detail in the article by Setsompop, Kawin, et al., "Blipped-controlled aliasing in parallel imaging for simultaneous multislice echo planar imaging with reduced g-factor penalty.", Magnetic Resonance in Medicine 67 (2012), 1210-1224. This method uses what is known as a multiband pulse to excite a plurality of slices simultaneously. In addition, the pulse waveforms for all the bands are summed, resulting in a multiband pulse modulated into a carrier band. For each excited slice, a linear phase ramp is added in k-space along the slice direction.

In order to reduce losses relating to the g-factor, offsets between the slices are produced during readout either by gradient blips on the slice axis or by modeling the phase of the RF pulses. After acquisition, the simultaneously excited slices are combined into a single slice. The slices may be separated from one another in post-processing using a slice-GRAPPA method (Setsompop et al., MRM 2012). If an acceleration is additionally applied in the slice plane, reconstruction in the slice plane is performed in a second act using the GRAPPA method.

The turbo-spin-echo (TSE) sequence is a sequence that is widely used in the clinical field for examining numerous body regions. The TSE sequence includes a plurality of echo sequences, with a plurality of phase encoding lines of the full k-space being acquired in each echo train after one excitation pulse. This is achieved by using refocusing pulses to refocus the spins after each readout line is acquired. Thus, compared with the conventional spin-echo (SE) sequence, the acquisition time is reduced by the number of refocused echoes in an echo sequence (what is known as the turbo factor).

To facilitate the separation of the combined multiband data, a reference scan is acquired in addition to the multiband data using a single band, which covers all the slices. Current SMS-TSE implementations contain a TSE or gradient-echo (GRE) reference scan before the acquisition of the SMS data. This reference scan is then used to perform both the calibration of the kernels for the slice-GRAPPA method and the calibration of the kernels for the GRAPPA method in the slice plane. After the slice-GRAPPA reconstruction is carried out for generating slice data of the slices, (which slice data is subsampled in k-space), calibration data for calculating the kernel of the slice-GRAPPA method is subsampled likewise. Reference lines are consequently deleted in the current implementation. For example, a reference scan for a SMS 2, iPAT 2 (R=2) acquisition includes 64 k-space lines. For the GRAPPA method in the slice plane, all the 64 reference lines may be used. For SMS, only 64/R=32 reference lines may be used. For iPAT 3 (R=3), only 64/3=21 reference lines may be used. This may lead to a reduced signal-to-noise ratio, separation artifacts and incorrect assignments of MR signals to the individual slices. The number of scanned reference lines may be increased to offset these disadvantages. This is inefficient, however, because the proportion of deleted data remains the same and yet the scan time is still extended. Besides the longer scan time, other disadvantages also arise, such as a greater probability that the patient moves during the reference scan, an increased SAR load, and, in the case of a TSE reference scan, $T_2$ decay and a reduced signal as a result.

U.S. Patent Application Publication No. 2016/0313433 A1 and U.S. Patent Application Publication No. 2015/0115958 A1 disclose simultaneous multislice measurement methods.

SUMMARY AND DESCRIPTION

The scope of the present disclosure is defined solely by the appended claims and is not affected to any degree by the statements within this description. The present embodiments may obviate one or more of the drawbacks or limitations in the related art.

An object of the present disclosure is to provide an improved method for calibration in a magnetic resonance imaging procedure, in which MR imaging data is acquired simultaneously from a multiplicity of slices of a subject under examination, wherein the method does not have the disadvantages mentioned above and has both a shorter scan time and improved MR image quality.

According to a first aspect, a method is provided for calibration in a magnetic resonance imaging procedure, in which MR imaging data is acquired simultaneously from a multiplicity of slices of a subject under examination. In one act, at least one reference dataset of an individual slice is provided, which reference dataset is fully sampled in k-space and includes a multiplicity of data points. In a further act, at least one calibration dataset is generated by rearranging an order of the data points in the at least one reference dataset. The at least one calibration dataset may contain substantially the same data points as the at least one reference dataset. In a further act, a reconstruction dataset, (which is used to assign MR imaging data to the individual slice), is calculated on the basis of the calibration dataset and in particular on the basis of the rearranged order of the data points in the at least one calibration dataset.

The method for calibration in a magnetic resonance imaging procedure, in which MR imaging data is acquired simultaneously from a multiplicity of slices of a subject under examination, has a higher signal-to-noise ratio, produces fewer artifacts in the separation of slice data, and exhibits fewer assignment errors in the separation of slice data than for conventional calibration methods, because a larger amount of data, (e.g., information), from a reference dataset is used for the calibration. This provides a more efficient calibration method, which provides a shorter examination time, and thus lower examination costs, and improved MR image quality compared with known calibration methods of MR imaging.

The method may also include shifting at least one k-space line from a first position in the order in the at least one reference dataset to a second position in the order. Shifting at least one k-space line from a first position in the order in the at least one reference dataset to a second position in the order allows more efficient and faster generation of a calibration dataset, which contains a larger number of data points of the reference dataset.

Calculating a reconstruction dataset may be performed using a calculation technique, in particular a sliding-window technique, which takes into account in the calculation the rearranged order of the data points in the at least one calibration dataset. Calculating a reconstruction dataset using a calculation technique, (e.g., a sliding-window technique), which takes into account in the calculation the rearranged order of the data points in the at least one calibration dataset allows more efficient and faster generation of a calibration dataset, which contains a larger number of data points of the reference dataset.

The method may further include using the reconstruction dataset to reconstruct at least one slice dataset from the MR imaging data, wherein the at least one slice dataset includes only MR imaging data from the individual slice and is subsampled in k-space. Using the reconstruction dataset to reconstruct at least one slice dataset, wherein the at least one slice dataset includes only MR imaging data from the individual slice and is subsampled in k-space, allows the MR imaging data to be assigned to each of the multiplicity of slices, resulting in a higher signal-to-noise ratio, fewer artifacts being produced, and fewer assignment errors.

A reference dataset may be provided for each slice, and at least one calibration dataset may be generated for each slice by rearranging an order of the data points in the corresponding reference dataset. Providing a reference dataset for each slice and generating at least one calibration dataset for each slice allows improved quality in assignment of the MR imaging data to each of the multiplicity of slices, resulting moreover in an even higher signal-to-noise ratio, fewer artifacts being produced and fewer assignment errors.

The data points of the reference dataset may be arranged in k-space in lines and rearranging an order of the data points in the reference dataset may include rearranging an order of the lines of the reference dataset. Rearranging an order of the lines of the reference dataset allows even more efficient and faster generation of a calibration dataset, which contains a larger number of data points of the reference dataset.

An order of the data points in the at least one reference dataset may be rearranged in the manner that the at least one calibration dataset is subsampled in k-space by the same factor as the MR imaging data originating from an individual slice. Subsampling the at least one calibration dataset in k-space by the same factor as the MR imaging data originating from an individual slice provides improved MR image quality, with an even greater signal-to-noise ratio and fewer artifacts being provided and fewer assignment errors being provided when assigning MR imaging data originating from the individual slice to a slice dataset.

Rearranging an order of the data points in the at least one reference dataset may include assigning the data points to at least two segments of the calibration dataset. The at least two segments may each be subsampled by the same factor as the MR imaging data originating from an individual slice. The rearrangement may also include attaching the at least two segments to one another. Assigning the data points to at least two segments of the calibration dataset allows more efficient and faster generation of a calibration dataset, which contains a larger number of data points of the reference dataset.

The imaging data originating from an individual slice may be subsampled in k-space by the factor a, and rearranging an order of the data points in the at least one reference dataset may include attaching a segments to one another, which segments have been subsampled by the factor a. Attaching segments a to one another, which segments have been subsampled by the factor a, allows more efficient and faster generation of a calibration dataset, which is subsampled by the factor a and contains a larger number of data points of the reference dataset.

Rearranging an order of the data points in the reference dataset may include arranging the $n^{th}$ lines in an $n^{th}$ segment for each value of $n=\{1, 2, \ldots, a\}$, and attaching the segments to one another. Arranging the $n^{th}$ lines in an $n^{th}$ segment for each value of $n=\{1, 2, \ldots, a\}$, and attaching the segments to one another, allows even better generation of a calibration dataset, which contains a larger number of data points of the reference dataset, for the case in which the slice datasets of the individual slices are subsampled by a factor a.

The MR imaging data originating from an individual slice may be subsampled in k-space by the factor 2 and rearranging an order of the data points in the reference dataset may include arranging the even lines in a first segment, arranging the odd lines in a second segment, and attaching the first segment and the second segment to one another. Arranging the even lines in a first segment, arranging the odd lines in a second segment, and attaching the first segment and the second segment to one another, allows more efficient and faster generation of a calibration dataset, which is subsampled by the factor 2 and contains a larger number of data points of the reference dataset.

The segments may be attached to one another in the phase encoding direction. Attaching the segments in the phase encoding direction allows faster generation of a calibration dataset, wherein in the transition region between the segments, data points having low energy in k-space, and thus a low weighting in the reconstruction, are arranged next to one another, resulting in fewer artifacts and fewer assignment errors in the reconstruction of slice datasets.

The segments may be attached to one another in the readout direction. Attaching the segments in the readout direction allows fast generation of a calibration dataset, wherein in the transition region between the segments, data points having a low energy in k-space, and thus a low weighting in the reconstruction, are arranged next to one another, resulting in fewer artifacts and fewer assignment errors in the reconstruction of slice datasets. Alternatively, it is also possible to attach a few segments attached to one another in the phase encoding direction, and to attach a few segments to one another in the readout direction.

A filter that reduces the intensity in k-space in the edge region of the segments may be applied to the individual segments. This may be performed, for instance, by a Gaussian filter or similar filter techniques known in the prior art. Applying a filter to the individual segments may further reduce the energy in k-space, and hence the weighting in the reconstruction of slice datasets, in the edge region of the segments.

A reference dataset may be provided on the basis of a single frequency band, thereby increasing the quality of the reference dataset.

Providing a reference dataset may be based on the turbo-spin-echo (TSE) technique or the gradient-echo (GRE) technique, thereby increasing the quality and the speed of the acquisition of the reference dataset.

In the method for calibration in a magnetic resonance imaging procedure, generating at least one calibration dataset may include generating at least two calibration datasets of an individual slice, with the data points of the at least one reference dataset being assigned to the at least two calibration datasets in such a way that an order of the data points in the reference dataset is changed. The at least two calibration datasets may each be subsampled by the same factor as the slice data from a slice. In addition, in the method, calculating a reconstruction dataset may include calculating at least two interim reconstruction datasets on the basis of the at least two calibration datasets, and averaging together the at least two interim reconstruction datasets to generate the reconstruction dataset.

Generating at least two calibration datasets of an individual slice, calculating at least two interim reconstruction datasets on the basis of the at least two calibration datasets, and averaging the at least two interim reconstruction datasets allows efficient and fast generation of a reconstruction dataset and provides a calibration method that has a higher signal-to-noise ratio, produces fewer artifacts and exhibits fewer assignment errors.

According to another aspect, a MR system for calibration in a magnetic resonance imaging procedure is provided, in which MR imaging data is acquired simultaneously from a multiplicity of slices of a subject under examination. The MR system includes a MR control unit and a memory unit, wherein the memory unit stores control information that may be executed by the MR control unit, and in addition, the MR system is designed to perform, when the control information is executed in the MR control unit, the following act. In one act, at least one reference dataset of an individual slice is provided, which reference dataset is fully sampled in k-space and includes a multiplicity of data points. In a further act, at least one calibration dataset is generated by rearranging an order of the data points in the at least one reference dataset. Moreover, the at least one calibration dataset may contain substantially the same data points as the at least one reference dataset. In a further act, a reconstruction dataset, which is used to assign MR imaging data to the individual slice, is calculated on the basis of the rearranged order of the data points in the at least one calibration dataset.

The MR system for calibration in a magnetic resonance imaging procedure, in which MR imaging data is acquired simultaneously from a multiplicity of slices of a subject under examination, may additionally be designed such that it performs the method according to one of the further aforementioned features when the control information is executed in the MR control unit.

For the MR system, for calibration in a magnetic resonance imaging procedure, in which MR imaging data is acquired simultaneously from a multiplicity of slices of a subject under examination, technical effects may be achieved that are comparable to the technical effects that were described above for the method according to the first aspect.

According to another aspect, a computer program product is provided which includes a program that may be loaded directly into a memory of a MR control unit of a MR system, and which is configured to perform the acts of the method corresponding to the features described under the first aspect when the program is executed in the MR control unit of the MR system.

According to another aspect, an electronically readable data storage medium is provided including electronically readable control information stored thereon, which information is designed such that it performs the method corresponding to the features described under the first aspect when the data storage medium is used in a MR control unit of a MR system.

The features presented above, which are described below, may be used not just in the corresponding explicitly presented combination but also in other combinations unless explicitly stated otherwise, or may be used individually, without departing from the scope of protection of the present disclosure.

BRIEF DESCRIPTION OF THE DRAWINGS

The disclosure is described in greater detail below with reference to the accompanying drawings.

DETAILED DESCRIPTION

Figure 1:
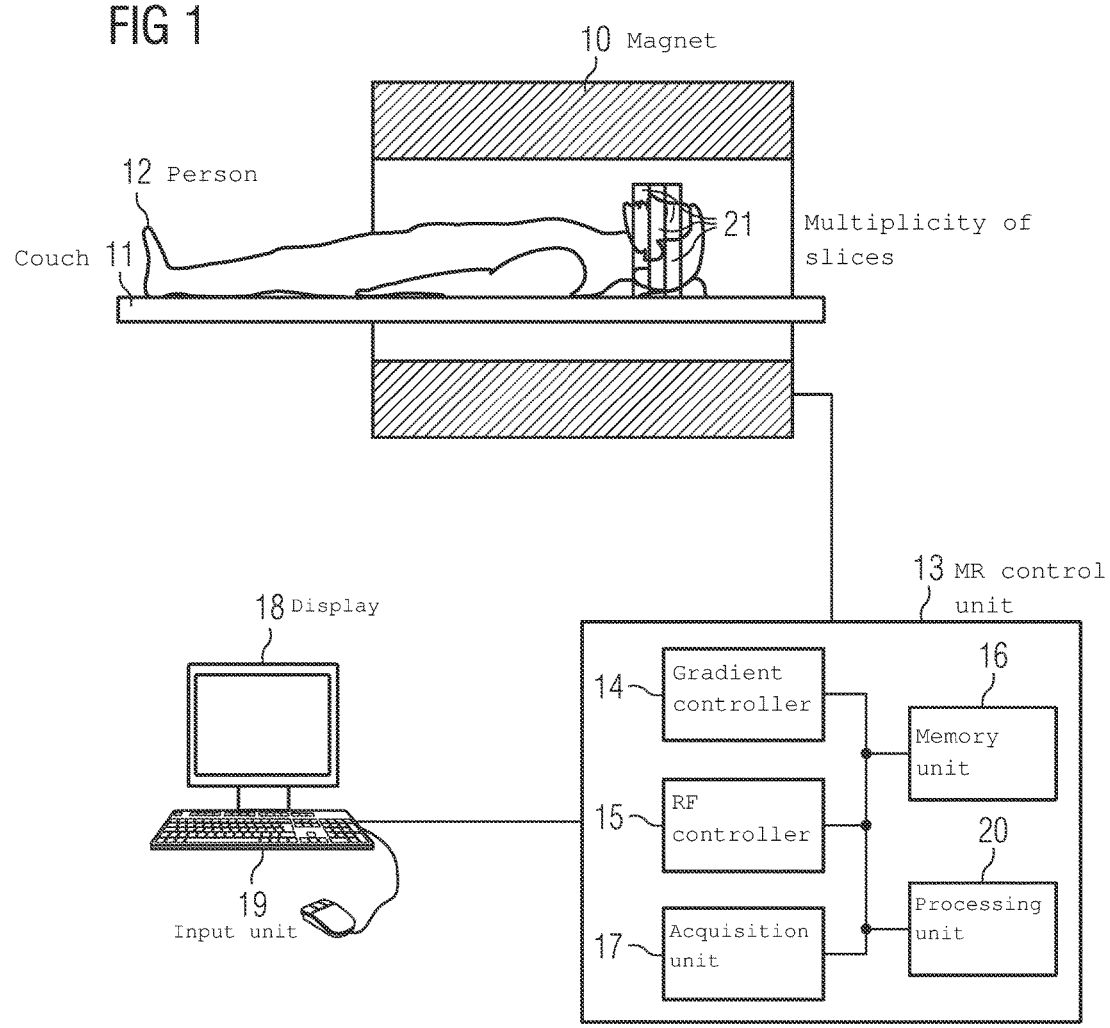
FIG. 1 depicts schematically an example of a MR system that may be used to perform a method for calibration in a magnetic resonance imaging procedure.

The present disclosure is described in greater detail below using embodiments with reference to the drawings. The same reference characters denote identical or similar elements in the FIGS. In addition, the FIGS. are schematic representations of various embodiments. Elements depicted in the FIGS. are not necessarily shown to scale. The elements shown in the FIGS. are instead depicted in a way that makes their function and purpose clear to a person skilled in the art. The connections shown in the FIGS. between functional units or other elements may also be implemented as an indirect connection, where a connection may be wireless or wired. Functional units may be implemented as hardware, software or a combination of hardware and software.

A magnetic resonance (MR) system is described with reference to FIG. 1, which system may be used, as explained below, to perform a calibration in SMS imaging.

A subject 12 under examination, (e.g., a person under examination), is moved into the tunnel of the system. The magnetic resonance system includes a magnet 10 for generating a main field B0, where a person 12 under examination arranged on a couch 11 is moved into the center of the magnet in order to acquire there, from a region under examination, spatially encoded magnetic resonance signals. The person 12 under examination includes a multiplicity of slices 21, which are excited simultaneously in a MR imaging procedure and from which MR imaging data is acquired simultaneously. The application of radio frequency pulses and the switching of magnetic field gradients may disrupt the magnetization produced by the main field B0 by deflecting the nuclear spins out of the equilibrium position, and the currents induced in receive coils during the return to the equilibrium position may be converted into magnetic resonance signals. Because a person skilled in the art knows in general how MR images are produced and how magnetic resonance signals are detected, this is not explained in greater detail.

The magnetic resonance system also includes a MR control unit 13, which is used to control the MR machine. The central MR control unit 13 is configured to perform the method described below for calibration in a magnetic resonance imaging procedure, in which MR imaging data is acquired simultaneously from a multiplicity of slices 21 of a subject under examination. The central MR control unit 13 includes a gradient controller 14 for controlling and switching the magnetic field gradients, and a radio frequency (RF) controller 15 for controlling and emitting the RF pulses for deflecting the nuclear spins from the equilibrium position. For example, the imaging sequences needed for acquiring the MR images, and the programs needed to operate the MR system, may be stored in a memory unit 16. An acquisition unit 17 controls the image acquisition and thus controls, on the basis of the selected imaging sequences, the sequence of the magnetic field gradients and RF pulses and the intervals for receiving MR signals. Therefore, the acquisition unit 17 also controls the gradient controller 14 and the RF controller 15. MR images, which may be displayed on a display 18, may be computed in a processing unit 20, while an operator may operate the MR system via an input unit 19. The memory unit 16 may include imaging sequences and program modules, which when executed in the processing unit 20 by one of the modules shown, perform the method. The RF controller 15 may also be designed to improve the calibration in a magnetic resonance imaging procedure, in which MR imaging data is acquired simultaneously from a multiplicity of slices 21 of a subject under examination, as explained in detail below. Specifically, the memory unit 16 stores for this purpose control information that may be executed by the MR control unit 13. In addition, the acquisition unit 17 is designed such that the acquisition unit 17 may perform the method described below for calibration in a magnetic resonance imaging procedure, in which MR imaging data is acquired simultaneously from a multiplicity of slices 21 of a subject under examination.

Figure 3:
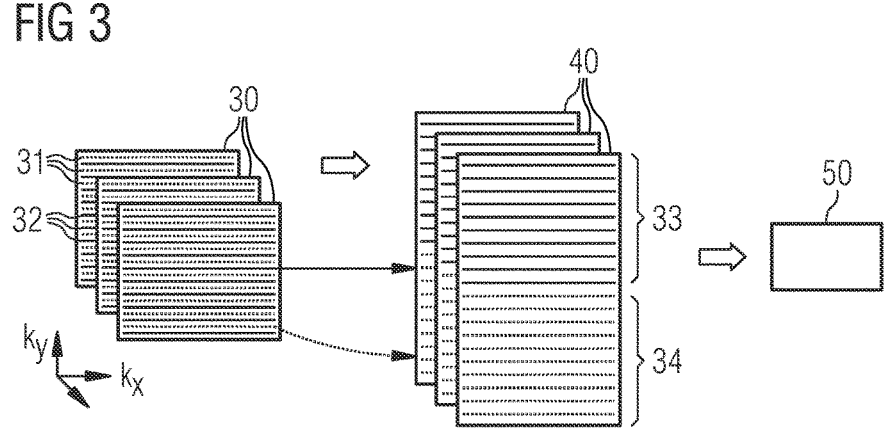
FIG. 3 depicts schematically a method for calibration in a magnetic resonance imaging procedure according to an exemplary embodiment.

The MR system of FIG. 1 is configured such that the MR system performs a calibration of the reconstruction datasets 50, (e.g., of slice-GRAPPA kernels), as shown in FIG. 3, when the control information is executed in the MR control unit 13.

Figure 2:
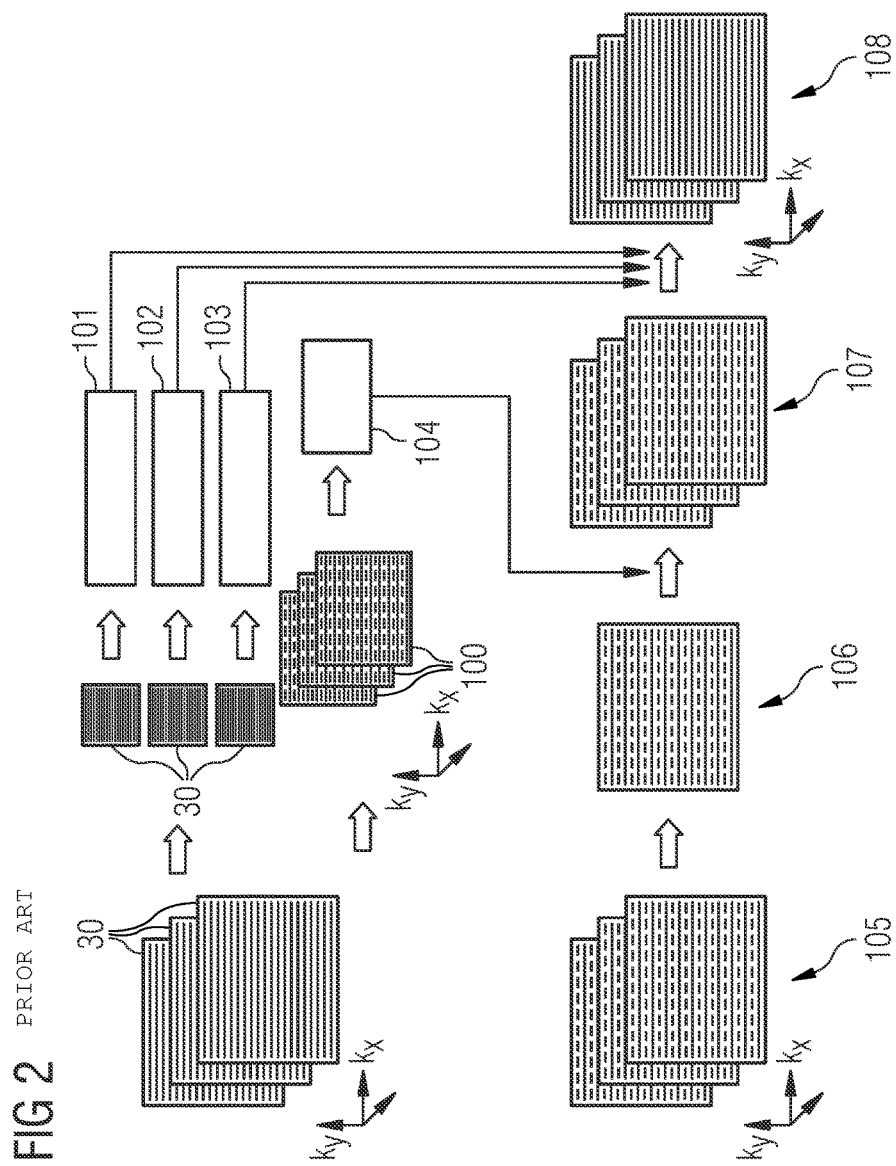
FIG. 2 depicts schematically a method for calibration in a magnetic resonance imaging procedure of the prior art.

FIG. 2 depicts schematically a method for calibration in a magnetic resonance imaging procedure of the prior art.

Three reference datasets 30 are provided, wherein each reference dataset 30 is assigned to a different slice 21 of a person 12 under examination and is fully subsampled in k-space. Each reference dataset 30 also includes a multiplicity of data points, which are each characterized by a kx-value, a ky-value and an intensity value, or else contrast value.

It shall be assumed that for a spacing of data points in k-space, the Nyquist theorem is satisfied if the spacing in the phase encoding direction equals 1 Δky (one times Δky). Additionally, 2 Δky (two times Δky) refers to subsampling once, etc. The reference datasets 30 are represented such that the kx-direction runs within the lines, and the ky-direction runs perpendicular to the lines, where kx is the readout direction and ky is the phase encoding direction. By sampling a slice 21 in full, a reference dataset 30 is filled with data points at a spacing of 1 Δky. For a subsampled acquisition by a factor 2, (e.g., subsampling once), the individual data points have a spacing of 2 Δky; correspondingly, for subsampling by the factor a, they have a spacing of a Δky. The data points in a reference dataset are additionally given in a specific order. In other words, the data points are given in a specific arrangement, arranged or sorted in a particular order, with the result that the data points are used sequentially in this order in the calculation of reconstruction datasets, in particular of slice-GRAPPA kernels.

Each reference dataset 30 also includes a multiplicity of lines in the ky-direction. The three reference datasets 30, which are fully sampled in k-space, are used to calculate in-plane GRAPPA kernels 101, 102, 103. In this process, the first reference dataset 30, which is fully sampled in k-space, is used to calculate a first in-plane GRAPPA kernel 101. The second reference dataset 30, which is fully sampled in k-space, is used to calculate a second in-plane GRAPPA kernel 102. The third reference dataset 30, which is fully sampled in k-space, is used to calculate a third in-plane GRAPPA kernel 103.

In addition, a slice-GRAPPA kernel 104 is also calculated from the three reference datasets 30. Subsampled calibration datasets 100 that have the same subsampling as the MR imaging data of the individual slices 21 are needed to calculate the slice-GRAPPA kernel 104. For this purpose, the reference datasets 30 are artificially subsampled, (e.g., subsequently changed into subsampled calibration datasets 100 such that they exhibit subsampling), where in particular for conventional calibration methods, data is deleted from the reference datasets 30 and not used again for the calibration. In the conventional calibration method of FIG. 2, every second line of the reference datasets 30 is deleted, (e.g., about half of the data is deleted from the reference datasets and not used for calibration of the slice-GRAPPA kernel 104). The resultant conventional calibration datasets 100 thus include only about half the data points of the reference datasets 30. In conventional calibration methods, the data points of the calibration datasets 100 are used sequentially in the calculation of the slice-GRAPPA kernel 104 in the order in which they are given in the calibration datasets 100.

The act 105 to 108 of FIG. 2 show a conventional SMS TSE calibration and reconstruction method. In act 105, three slices 21 of a person 12 under examination are excited simultaneously. In act 106, a combined acquisition of MR imaging data from the three slices 21 is performed. In act 107, a slice-GRAPPA method is performed using the slice-GRAPPA kernel 104, in which process a slice dataset, which includes only MR imaging data from one of the slices 21, is reconstructed for each of the three slices 21. In act 108, an in-plane GRAPPA method using the three in-plane GRAPPA kernels 101, 102 and 103 is applied to the MR imaging data from the individual three slices 21, in which process complete MR imaging data for the individual three slices 21 is reconstructed.

FIG. 3 depicts schematically a method for calibration in a magnetic resonance imaging procedure according to an exemplary embodiment.

Three reference datasets 30 are provided, wherein each reference dataset 30 is assigned to a different slice 21 of a person 12 under examination and is fully subsampled in k-space. Each reference dataset 30 also includes a multiplicity of lines in the ky-direction, where each reference dataset 30 also includes a multiplicity of odd lines 31 and a multiplicity of even lines 32. The data points are given in a specific order within the reference dataset 30. By rearranging an order of the data points of each reference dataset 30, a corresponding calibration dataset 40 is produced from each reference dataset 30. In this process, the reference lines of a reference dataset 30 are rearranged within the reference dataset 30 in a rearranged order, with the odd lines 31 of the reference dataset 30 being arranged in a first segment 33, the even lines 32 of the reference dataset 30 being arranged in a second segment 34, and the second segment 34 being attached to the first segment 33 to generate the corresponding calibration dataset 40. As a result, the generated calibration dataset 40 is subsampled once. A reconstruction dataset 50 is calculated from the generated three calibration datasets 40. In this process, the data points are processed sequentially according to the rearranged order of the calibration datasets 40 in accordance with methods known from the prior art for calculating slice-GRAPPA kernels. In particular, a sliding-window technique may be performed here, which takes into account the rearranged order of the data points in the calibration datasets 40.

The described method for calibration is based on the fact that the MR imaging data of a slice 21 has been acquired using an in-plane acceleration factor of 2, and therefore is subsampled once. Therefore, the calibration data in the calibration dataset 40 is also subsampled once. In an iPAT 3 scan, three segments, for example, would accordingly be joined to one another, (e.g., attached to one another).

Figure 4:
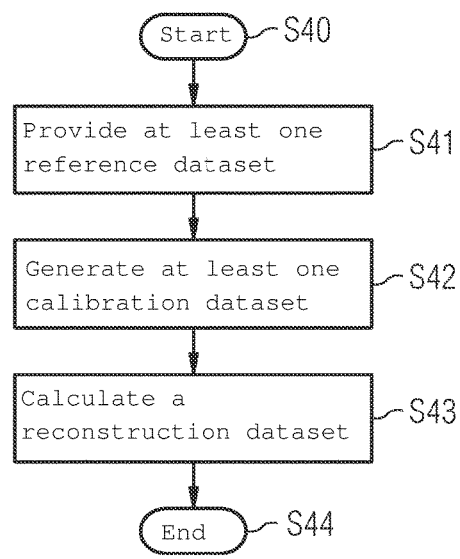
FIG. 4 depicts schematically a flow diagram containing acts that are performed for calibration in a magnetic resonance imaging procedure according to an exemplary embodiment.

FIG. 4 depicts schematically a flow diagram containing acts that are performed for calibration in a magnetic resonance imaging procedure according to an exemplary embodiment.

The method starts in act S40. In act S41, at least one reference dataset 30 is provided for a slice 21 of a person 12 under examination, wherein the reference dataset 30 is fully sampled in k-space and includes a multiplicity of data points. In act S42, at least one calibration dataset 40 is generated by rearranging an order of the data points in the at least one reference dataset 30. In act S43, a reconstruction dataset 50, which is used to assign MR imaging data to the individual slice 21, is calculated on the basis of the rearranged order of the data points in the at least one calibration dataset 40. The method ends in act S44.

To summarize, a method is provided for calibration in a MR imaging procedure, in which MR imaging data is acquired simultaneously from a multiplicity of slices of a subject under examination. In this method, at least one subsampled calibration dataset is generated from a fully sampled reference dataset of an individual slice by rearranging an order of the data points in the reference dataset. In addition, a reconstruction dataset, which is used to assign MR imaging data to the individual slice, is calculated on the basis of the rearranged order of the data points in the at least one calibration dataset. In this process, the MR imaging data from the individual slice is subsampled in k-space.

The method for calibration in a MR imaging procedure, in which MR imaging data is acquired simultaneously from a multiplicity of slices of a subject under examination, has a higher signal-to-noise ratio, produces fewer artifacts in the separation of slice data, and exhibits fewer assignment errors in the separation of slice data, because a larger number of data points, in other words information, from a reference dataset is used. This increases the efficiency and the image quality of the MR imaging procedure of the calibration method compared with known calibration methods of MR imaging.

It is to be understood that the elements and features recited in the appended claims may be combined in different ways to produce new claims that likewise fall within the scope of the present disclosure. Thus, whereas the dependent claims appended below depend from only a single independent or dependent claim, it is to be understood that these dependent claims may, alternatively, be made to depend in the alternative from any preceding or following claim, whether independent or dependent, and that such new combinations are to be understood as forming a part of the present specification.

While the present disclosure has been described above by reference to various embodiments, it may be understood that many changes and modifications may be made to the described embodiments. It is therefore intended that the foregoing description be regarded as illustrative rather than limiting, and that it be understood that all equivalents and/or combinations of embodiments are intended to be included in this description.

The invention claimed is:

1. A method for calibration in a magnetic resonance (MR) imaging procedure, in which MR imaging data is acquired simultaneously from a multiplicity of slices of a subject under examination, the method comprising:
   providing at least one reference dataset of an individual slice, wherein the at least one reference dataset is fully sampled in k-space and comprises a multiplicity of data points;
   generating, by a MR control unit, at least one calibration dataset by rearranging an order of the data points in the at least one reference dataset; and
   calculating, by the MR control unit, a reconstruction dataset, which is used to assign MR imaging data to the individual slice, based on the rearranged order of the data points in the at least one calibration dataset.

2. The method of claim 1, wherein the generating of the at least one calibration dataset further comprises shifting at least one k-space line from a first position in the order in the at least one reference dataset to a second position in the order.

3. The method of claim 1, wherein the calculating of the reconstruction dataset is performed using a sliding-window technique, which takes into account the rearranged order of the data points in the at least one calibration dataset.

4. The method of claim 1, further comprising:
   using the reconstruction dataset to reconstruct at least one slice dataset from the MR imaging data, wherein the at least one slice dataset comprises only MR imaging data from the individual slice and is subsampled in k-space.

5. The method of claim 1, wherein the providing of the at least one reference dataset comprises providing a reference dataset for each slice, and
   wherein the generating of the at least one calibration dataset comprises generating a calibration dataset for each slice by rearranging an order of the data points in the corresponding reference dataset.

6. The method of claim 1, wherein the data points of the at least one reference dataset are arranged in k-space in lines, and
   wherein the rearranging of the order of the data points in the at least one reference dataset comprises rearranging an order of the lines of the at least one reference dataset.

7. The method of claim 1, wherein the order of the data points in the at least one reference dataset is rearranged in a manner that the at least one calibration dataset is subsampled in k-space by a same factor as the MR imaging data originating from the individual slice.

8. The method of claim 1, wherein the rearranging of the order of the data points in the at least one reference dataset comprises assigning the data points to at least two segments of the calibration dataset.

9. The method of claim 1, wherein the MR imaging data originating from the individual slice is subsampled in k-space by factor a, and
wherein the rearranging of the order of the data points in the at least one reference dataset comprises attaching segments a to one another, which segments have been subsampled by the factor a.

10. The method of claim 9, wherein the rearranging of the order of the data points in the at least one reference dataset further comprises:
arranging $n^{th}$ lines in an $n^{th}$ segment for each value of n={1, 2, . . . , a}; and
attaching the segments to one another.

11. The method of claim 8, wherein the MR imaging data originating from the individual slice is subsampled in k-space by a factor of 2, and
wherein rearranging the order of the data points in the at least one reference dataset comprises:
arranging even lines in a first segment;
arranging odd lines in a second segment; and
attaching the first segment and the second segment to one another.

12. The method of claim 9, wherein the segments are attached to one another in a phase encoding direction.

13. The method of claim 9, wherein the segments are attached to one another in a readout direction.

14. The method of claim 8, wherein a filter that reduces an intensity in k-space in an edge region of the segments is applied to the individual segments.

15. The method of claim 1, wherein the at least one reference dataset is provided based on a single frequency band.

16. The method of claim 1, wherein the providing of the at least one reference dataset is based on a turbo-spin-echo technique or a gradient-echo technique.

17. The method of claim 1, wherein the generating of the at least one calibration dataset comprises generating at least two calibration datasets of the individual slice, and
wherein the calculating of the reconstruction dataset comprises calculating at least two interim reconstruction datasets based on the at least two calibration datasets, and averaging together the at least two interim reconstruction datasets to generate the reconstruction dataset.

18. A magnetic resonance (MR) system for calibration in a magnetic resonance imaging procedure, in which MR imaging data is acquired simultaneously from a multiplicity of slices of a subject under examination, the MR system comprising:
a magnetic resonance (MR) control unit; and
a memory unit,
wherein the memory unit stores control information configured to be executed by the MR control unit, and
wherein the MR system is configured to, when the control information is executed in the MR control unit, at least perform:
provide at least one reference dataset of an individual slice, wherein the at least one reference dataset is fully sampled in k-space and comprises a multiplicity of data points;
generate at least one calibration dataset by rearranging an order of the data points in the at least one reference dataset; and
calculate a reconstruction dataset, which is used to assign MR imaging data to the individual slice, based on the rearranged order of the data points in the at least one calibration dataset.

19. The MR system of claim 18, wherein the MR system is further configured to, when the control information is executed in the MR control unit, at least perform:
use the reconstruction dataset to reconstruct at least one slice dataset from the MR imaging data, wherein the at least one slice dataset comprises only MR imaging data from the individual slice and is subsampled in k-space.

20. A computer program product which comprises a program configured to be loaded directly into a memory of a magnetic resonance (MR) control unit of a MR system, wherein the computer program product, when the program is executed in the MR control unit of the MR system, is configured to at least perform:
provide at least one reference dataset of an individual slice, wherein the at least one reference dataset is fully sampled in k-space and comprises a multiplicity of data points;
generate at least one calibration dataset by rearranging an order of the data points in the at least one reference dataset; and
calculate a reconstruction dataset, which is used to assign MR imaging data to the individual slice, based on the rearranged order of the data points in the at least one calibration dataset.

\* \* \* \* \*